United States Patent [19]

Iwashita

[11] Patent Number: 4,655,257
[45] Date of Patent: Apr. 7, 1987

[54] GUIDE TUBE ASSEMBLY FOR INDUSTRIAL ENDOSCOPE

[75] Inventor: Yoshiyuki Iwashita, Tokyo, Japan

[73] Assignee: Kabushiki Kaisha Machida Seisakusho, Tokyo, Japan

[21] Appl. No.: 793,745

[22] Filed: Nov. 1, 1985

[30] Foreign Application Priority Data

Mar. 25, 1985 [JP] Japan .............................. 60-41613[U]

[51] Int. Cl.[4] .............................................. A61B 1/00
[52] U.S. Cl. ......................................... 138/120; 128/4
[58] Field of Search ................. 138/120, 155; 128/4-8; 356/241

[56] References Cited

U.S. PATENT DOCUMENTS

| 3,557,780 | 1/1971 | Sato ......................................... 128/4 |
| 3,572,325 | 3/1971 | Bazell et al. .......................... 138/120 |
| 3,583,393 | 6/1971 | Takahaski ................................ 128/4 |
| 4,294,233 | 10/1981 | Takahaski ................................ 128/4 |
| 4,351,323 | 9/1982 | Ouchi et al. ............................. 128/4 |

FOREIGN PATENT DOCUMENTS

| 2752325 | 7/1978 | Fed. Rep. of Germany .......... 128/4 |
| 2809741 | 9/1978 | Fed. Rep. of Germany .......... 128/4 |
| 52-5194 | 10/1977 | Japan ..................................... 128/4 |

Primary Examiner—Stephen Marcus
Assistant Examiner—Leo J. Peters
Attorney, Agent, or Firm—Kane, Dalsimer, Kane, Sullivan and Kurucz

[57] ABSTRACT

A guide tube assembly for an industrial endoscope comprises a multiplicity of tube segments arranged to form therein a long guide bore. A hand actuator is connected to a proximal one of the tube segments. At least one pair of elongated members have their respective one ends fixedly secured to a distal one of the tube segments, and extend through communication bores formed in the remaining tube segments to the hand actuator. A resilient member is mounted on the hand actuator for resiliently pulling the elongated members to bias the tube segments so as to bring them into contact with each other.

8 Claims, 6 Drawing Figures

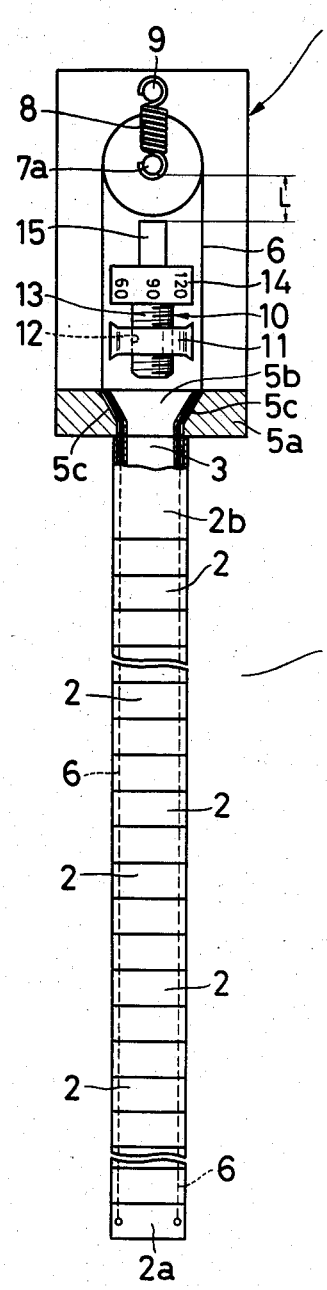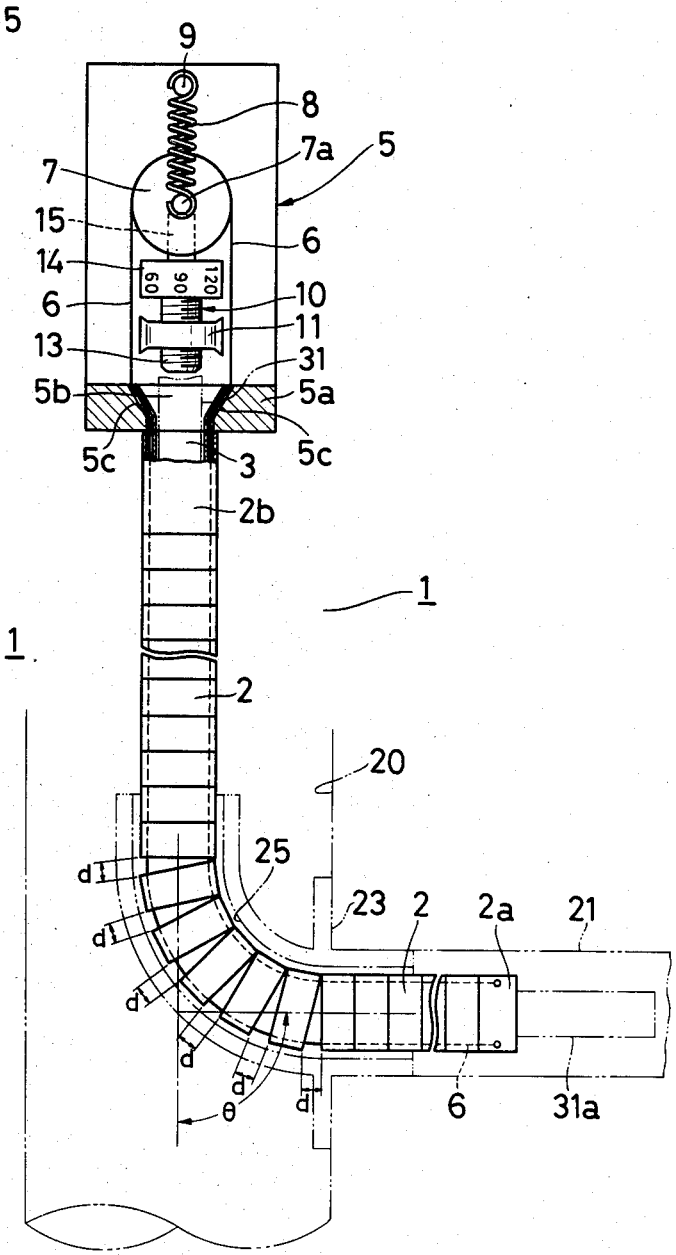

GUIDE TUBE ASSEMBLY FOR INDUSTRIAL ENDOSCOPE

BACKGROUND OF THE INVENTION

Field of the Invention

The present invention relates to a guide tube assembly for an industrial endoscope.

BRIEF DESCRIPTION OF THE DRAWINGS

FIG. 1 is a partially cross-sectional, side elevational view of a guide tube assembly for an industrial endoscope in accordance with an embodiment of the present invention;

FIG. 2 is a view similar to FIG. 1, but showing the guide tube assembly curved at right angles;

FIGS. 5 and 6 are fragmental cross-sectional view showing conventional manners in which an endoscope is utilized to observe an interior of a piping or the like.

RELATED ART STATEMENT

Figure 5:
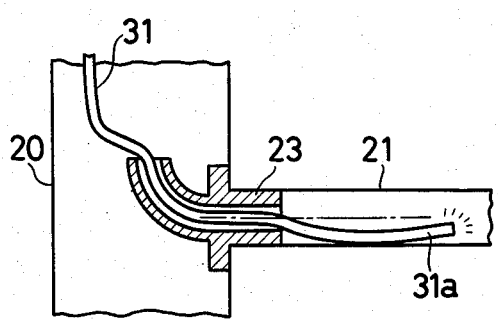
Figure 6:
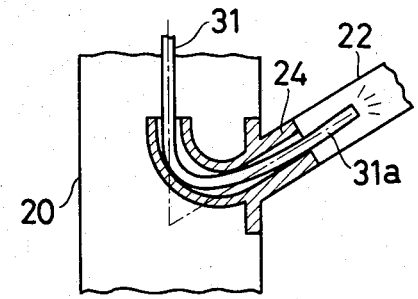

An industrial endoscope has been utilized to observe an interior of an industrial piping or the like. As shown in FIGS. 5 and 6, for example, when it is desired to observe an interior of a small diameter piping 21 or 22 branching in an inclined manner at right angles or at an angle greater than 90 degrees from an intermediate portion of a long, large diameter piping 20, a guide tube 23 or 24 is previously fitted in the branch between the pipings 20 and 21 or 22. Subsequently, an inserting portion 31 of the industrial endoscope is remote-controlled so as to be inserted in and pressed into the guide tube 23 or 24, to thereby be guided into the small diameter piping 21 or 22. The inserting portion 31 of the industrial endoscope is formed of a flexible tube or the like and has a considerable flexibility.

However, since the inserting portion 31 is flexible, it has been difficult to operate the inserting portion 31 so as to locate a tip thereof in position to insert the tip into the guide tube 23 or 24. In addition, as shown in FIG. 5, when it is desired to observe the interior of the small diameter piping 21 inclined at right angles, the inserting portion 31 inserted into the small diameter piping 21 cannot be maintained in a straightened condition, but is located on the bottom of the piping 21. Accordingly, should a distal end 31a of the inserting portion 31, which is capable of being curved, be curved by the remote control, it would be impossible to observe the bottom of the piping 21. In this manner, the observation has had a limitation or restriction in the field of view. Moreover, when it is desired to observe the interior of the small diameter piping 22 inclined at an angle greater than 90 degrees as shown in FIG. 6, the inserting portion 31 is bent within the guide tube 24 because of the flexibility of the inserting portion 31, and it is impossible to transmit the pressing force at an operator's hand to the inserting portion 31. Thus, it has been difficult to guide the inserting portion 31 into the interior of the piping 22.

OBJECT AND SUMMARY OF THE INVENTION

An object of the present invention is to provide a guide tube assembly for an industrial endoscope, comprising: a multiplicity of tube segments including a distal end tube segment and a proximal end tube segment and arranged to form therein a long guide bore, each of the tube segments including the proximal end segment having therein at least one pair of communication bores; a hand actuator connected to the proximal end tube segment; at least one pair of elongated members having their respective one ends fixedly secured to the distal end tube segment, the at least one pair of elongated members respectively extending through the at least one pair of communication bores in each of the tube segments including the proximal end tube segment, to the hand actuator; and resilient means mounted on the hand actuator for resiliently pulling the elongated members to bias the multiplicity of tube segments so as to bring them into contact with each other.

DETAILED DESCRIPTION OF THE PREFERRED EMBODIMENT

The present invention will now be described by way of an example with reference to FIGS. 1 to 4 of the accompanying drawings.

Figure 3:
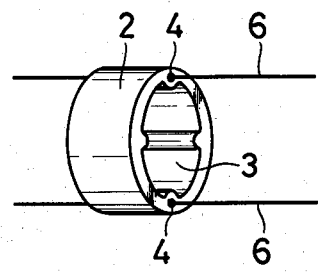
FIG. 3 is a perspective view of a tube segment shown in FIGS. 1 and 2.

Referring first to FIGS. 1 through 3, a guide tube assembly for guiding an inserting portion 31 of an endoscope, in accordance with an embodiment of the present invention, is generally designated by the reference numeral 1. The guide tube assembly 1 comprises a multiplicity of tube segments 2 which include a distal end tube segment 2a and a proximal end tube segment 2b. The tube segments 2, 2a and 2b are arranged so as to form therein a long guide bore 3 into which the inserting portion 31 is adapted to be inserted. In addition, as shown in FIG. 3, a pair of diametrically opposed communication bores 4 and 4 are formed in each of the tube segments 2 and 2b except for the distal end tube segment 2a.

A L-shaped hand actuator 5 has one end 5a thereof which is secured to the proximal end tube segment 2b. The one end 5a has a bore 5b formed at a center thereof, having a diameter substantially the same as that of the guide bore 3, and a pair of communication bores 5c and 5c communicating with the pair of communication bores 4 and 4, respectively. The inserting portion 31 of the endoscope is adapted to be inserted into the guide bore 3 from the bore 5b.

The end 5a of the hand actuator 5 may not be fixedly secured to the proximal end tube segment 2b.

A pair of elongated members or wires 6 and 6 have their respective one ends secured to the distal end tube segment 2a. The wires 6 and 6 extend from the distal end tube segment 2a through the pair of communication bores 4 and 4 in the tube segments 2 and 2b and through the pair of communication bores 5c and 5c in the end 5a of the hand actuator 5, respectively, so as to have the other ends located at the hand actuator 5. The respective other ends of the wires 6 are connected to each other to form a U-shaped loop trained around a drum 7 which is rotatably supported on a support pin 7a. The end of the support pin 7a is inserted into a slit (not shown) formed in the wall of the hand actuator 5. A couple of flanges (not shown) are secured to the end of the support pin 7a. Each of the flanges abut against the opposite surfaces of the wall of the hand actuator 5, respectively. Therefore the support pin 7a is supported on the hand actuator 5 so as to be slidable longitudinally thereof toward and away from the one end 5a of the hand actuator 5.

A resilient member or coil spring 8 has one end thereof supported by a pin 9 at the other end of the hand actuator 5 and the other end supported by the support pin 7a of the drum 7. The wires 6 are pulled by the coil spring 8 through the drum 7.

The hand actuator 5 has mounted thereon an adjustable stopper mechanism 10 which comprises a bracket 11 fixed to the hand actuator 5 and having a threaded bore 12, a threaded rod 13 threadedly engaging the threaded bore 12, an operating dial 14 fixedly secured to an end of the threaded rod 13, and a rod 15 secured to an end face of the dial 14 opposite the threaded rod 13 and extending from the dial 14 toward the support pin 7a in coaxial relation to the threaded rod 13. The support pin 7a of the drum 7 is adapted to abut against or engage the free end of the rod 15.

With the guide tube assembly 1 constructed as described above, as shown in FIG. 1, the wires 6 are pulled by the tension force of the coil spring 8 to cause the distal end tube segment 2a to be drawn toward the hand actuator 5, so that the multiplicity of arranged tube segments 2, 2a and 2b are brought into contact with each other in a straightened condition. The inserting portion 31 of the industrial endoscope is previously inserted into the long guide bore 3 formed by the multiplicity of tube segments 2, 2a and 2b.

Description will now be made to a case where the guide tube assembly 1 is utilized to observe an interior of a small diameter piping 21 branching at an angle $\theta = 90$ degrees from an intermediate portion of a long, large diameter piping 20 indicated by the two-dot-and-dash line in FIG. 2. At the outset, a guide tube 23 is previously fitted in the branch between the pipings 20 and 21, by means of an industrial robot or the like. The guide tube 23 has therein a guide bore 25 curved at 90 degrees.

Subsequently, the operating dial 14 is actuated and rotated to cause the graduations on the dial 14 to be brought into registration with 90 degrees, to thereby set the position of the rod 15. This allows the drum 7 to slide toward the rod 15 by a distance L, whereupon the free end of the rod 15 facing to the support pin 7a is engaged by the support pin 7a to limit the further sliding movement of the support pin 7a toward the one end 5a of the hand actuator 5. With such condition, the guide tube assembly 1 is inserted into the guide bore 25. At this time, since the tube segments 2, 2a and 2b are maintained in a straightened condition with a predetermined strength by the coil spring 8, it is possible to easily insert the tip of the guide tube assembly 1 into the guide bore 25, in spite of the fact that the guide tube assembly 1 is long in length.

Several tube segments 2 located within the guide bore 25 are generally curved at 90 degrees along the guide bore 25, so that each pair of adjacent tube segments 2 are brought into contact with each other at an inward peripheral side with respect to the curved line and are spaced from each other a distance d at an outward peripheral side with respect to the curved line. The wire 6 located at the outword peripheral side and extending from the one end 5a of the hand actuator 5 extended by a distance corresponding to the sum of the distances d. That is, the drum 7 is moved toward the rod 15 against the tension force of the coil spring 8 by a distance corresponding to the half of the extended distance of the wire 6, and the support pin 7a abuts against the rod 15. The abutment of the support pin 7a against the rod 15 prevents the wire 6 from being further extended, so that the tube segments 2 are as a whole curved only within the guide tube 23, but are inhibited from being curved at the other locations. Accordingly, as the tube segments 2 and 2a come out of the guide tube 23 and enter the small diameter piping 21, the tube segments 2 and 2a are again brought into a straightened condition, and the straightened condition is maintained by a strong force corresponding to the tension strength on the wires 6. Consequently, should the inserting portion 31 of the industrial endoscope be formed of a flexible tube or the like and have a considerable flexibility, it would be possible to locate the inserting portion 31 substantially at a center of the small diameter piping 21, because the inserting portion 31 would be supported by the guide tube assembly 1 under the straightened condition. Thus, it is possible to curve a distal end 31a of the inserting portion 31, which is capable of being curved and extends from the guide tube assembly 1, in an omnidirectional manner by the remote control, and it is possible to widen the field of view of the endoscope.

Additionally, when the angle $\theta$ of the small diameter piping 22 with respect to the large diameter piping 20 is 120 degrees, for example, a guide tube 24 having therein a guide bore curved at 120 degrees is utilized. The operating dial 14 is actuated and rotated to cause the graduations thereon to be brought into registeration with 120 degrees, to thereby adjust the position of the rod 15. In this case, the distance L through which the drum 7 can slide is increased as compared with the case of 90 degrees described above. In this case, too, the support pin 7a abuts against the rod 15 at the time the distal end tube segment 2a passes over the curved section of the guide tube 24. The guide tube assembly 1 can be easily inserted into the small diameter piping 22 in a manner similar to that described above.

Figure 4:
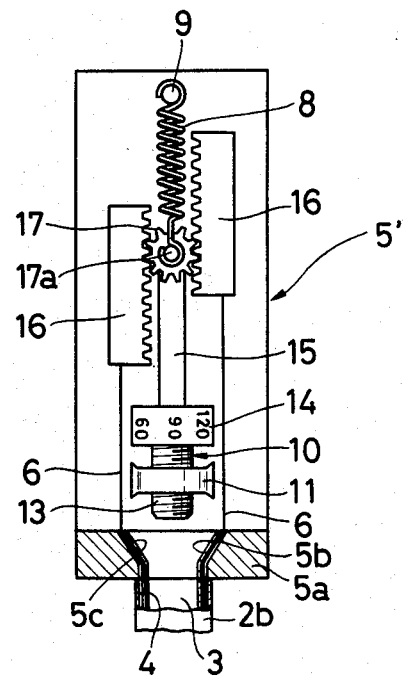
FIG. 4 is a side elevational view of a modification of a hand actuator.

FIG. 4 shows a modification of the hand actuator, which is generally designated by the reference numeral 5'. In the hand actuator 5', a pair of spaced parallel racks 16 and 16 and a single pinion 17 disposed therebetween and in mesh therewith are utilized in substitution for the drum 7 used in the previous embodiment. The racks 16 and 16 are movable along the hand actuator 5' toward and away from the proximal end tube segment 2b. The wires 6 and 6 have their respective other ends fixedly secured to the pair of racks 16 and 16, respectively. A support pin 17a on which the pinion 17 is rotatably mounted is supported by an end of the coil spring 8, and is adapted to abut against or engage the rod 15 of the adjustable stopper mechanism 10.

The present invention should not be limited to the above-mentioned embodiment and modification, but it should be understood that the present invention can be embodied in various other manners. For example, an additional pair of communication bores may be formed in each of the tube segments to allow an additional pair of wires to pass through the additional pair of communication bores, respectively. Furthermore, although the embodiment has been described in which the inserting portion of the endoscope is separate from the guide tube assembly, they may be connected in unison with each other. Moreover, the partially straightened condition of the tube segments may be maintained only by the tension force of the resilient member or coil spring, without the utilization of the adjustable stopper mechanism.

As described above, since the guide tube assembly for the industrial endoscope in accordance with the present invention is constructed such that the multiplicity of arranged tube segments can be maintained in a straightened condition by the resilient member, even when it is desired, for example, to observe an interior of a small diameter piping inclined at any angle with respect to a large diameter piping such as an industrial piping or the like, it is possible to insert the guide tube assembly into a guide tube disposed at a branch between the small and large diameter pipings, so that it is possible to easily guide the inserting portion of the industrial endoscope. In addition, because the guide tube assembly can be maintained in the straightened condition even within the small diameter piping, it is possible to widen the field of view of the observation by the endoscope.

What is claimed is:

1. A guide tube assembly for an industrial endoscope, comprising:
   a multiplicity of tube segments including a distal end tube segment and a proximal end tube segment and arranged to form therein a long guide bore, each of said tube segments including said proximal end tube segment having therein at least one pair of communication bores;
   a hand actuator connected to said proximal end tube segment, said hand actuator having one end thereof connected to said proximal end tube segment, said hand actuator having mounted thereon a rotatable drum movable along said hand actuator toward and away from said one end thereof, said pair of elongated members having their respective other ends connected to each other to form a loop trained around said drum, said resilient means biasing said drum away from said one end of said hand actuator, said hand actuator including a support pin mounted thereon so as to be slidable along said hand actuator, said drum being mounted on said support pin so as to be rotatable around an axis thereof, said resilient means comprising a coil spring having one end thereof connected to said support pin and the other end connected to said hand actuator;
   at least one pair of elongated members having their respective one ends fixedly secured to said distal end tube segment, said at least one pair of elongated members respectively extending through said at least one pair of communication bores in each of said tube segments including said proximal end tube segment, to said hand actuator; and
   resilient means mounted on said hand actuator for resileintly pulling said elongated members to bias said multiplicity of tube segments so as to bring them into contact with each other.

2. A guide tube assembly as defined in claim 1, including adjustable stopper means mounted on said hand actuator for limiting the sliding movement of said support pin toward said one end of said hand actuator.

3. A guide tube assembly as defined in claim 2, wherein said adjustable stopper means comprises a threaded rod member having one end thereof facing to said support pin and threadably engaging said hand actuator so as to be movable threalong toward and away from said support pin upon the rotation of said threaded rod member, to thereby adjust a distance between said one end of said threaded rod member and said support pin, said one end of said threaded rod member being engaged by said support pin when the same is slid toward said one end of said hand actuator, to limit the sliding movement of said support pin.

4. A guide tube assembly as defined in claim 3, wherein said adjustable stopper means further comprises a graduated dial mounted on said threaded rod member for rotation therewith.

5. A guide tube assembly for an industrial endoscope, comprising:
   a multiplicity of tube segments including a distal end tube segment and a proximal end tube segment and arranged to form therein a long guide bore, each of said tube segments including said proximal end tube segment having therein at least one pair of communication bores;
   a hand actuator connected to said proximal end tube segment, said hand actuator having one end thereof connected to said proximal end tube segment, said hand actuator including a pair of spaced parallel racks mounted threon so as to be slidable along said hand actuator toward and away from said one end thereof, and a pinion disposed between said pair of racks in mesh therewith, said resilient means biasing said pinion away from said one end of said hand actuator, said pair of elongated members having their respective other ends connected to said pair of racks, respectively, said hand actuator including a support pin mounted thereon so as to be slidable along said hand actuator, said pinion being mounted on said support pin so as to be rotatable around an axis thereof; said resilient means comprising a coil spring having one end thereof connected to said support pin and the other end connected to said hand actuator;
   at least one pair of elongated members having their respective one ends fixedly secured to said distal end tube segment, said at least one pair of elongated members respectively extending through said at least one pair of communication bores in each of said tube segments including said proximal end tube segment, to said hand actuator; and
   resilient means mounted on said hand actuator for resiliently pulling said elongated members to bias said multiplicity of tube segments so as to bring them into contact with each other.

6. A guide tube assembly as defined in claim 5, including adjustable stopper means mounted on said hand actuator for limiting the sliding movement of said support pin toward said one end of said hand actuator.

7. A guide tube assembly as defined in claim 6, wherein said adjustable stopper means comprises a threaded rod member having one end thereof facing to said support pin and threadedly engaging said hand actuator so as to be movable therealong toward and away from said support pin upon the rotation of said threaded rod member, to thereby adjust a distance between said one end of said threaded rod member and said support pin, said one end of said threaded rod member being engaged by said support pin when the same is slid toward said one end of said hand actuator, to limit the sliding movement of said support pin.

8. A guide tube assembly as defined in claim 7, wherein said adjustable stopper means further comprises a graduated dial mounted on said threaded rod member for rotation therewith.

* * * * *